(12) United States Patent
Williams

(10) Patent No.: US 10,507,039 B2
(45) Date of Patent: Dec. 17, 2019

(54) ADAPTER ASSEMBLY INCLUDING A REMOVABLE TROCAR ASSEMBLY

(71) Applicant: Covidien LP, Mansfield, MA (US)

(72) Inventor: Justin Williams, Southbury, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 16/171,468

(22) Filed: Oct. 26, 2018

(65) Prior Publication Data

US 2019/0059934 A1 Feb. 28, 2019

Related U.S. Application Data

(63) Continuation of application No. 14/865,602, filed on Sep. 25, 2015, now Pat. No. 10,111,684.

(51) Int. Cl.
| | |
|---|---|
| *A61B 17/072* | (2006.01) |
| *A61B 17/34* | (2006.01) |
| *A61B 17/115* | (2006.01) |
| *A61B 17/068* | (2006.01) |
| *A61B 17/064* | (2006.01) |
| *A61B 17/00* | (2006.01) |
| *A61B 90/00* | (2016.01) |

(52) U.S. Cl.
CPC ........ *A61B 17/3417* (2013.01); *A61B 17/072* (2013.01); *A61B 17/115* (2013.01); *A61B 17/1155* (2013.01); *A61B 17/068* (2013.01); *A61B 17/0644* (2013.01); *A61B 17/07207* (2013.01); *A61B 2017/0046* (2013.01); *A61B 2017/00464* (2013.01); *A61B 2017/00473* (2013.01); *A61B 2017/00477* (2013.01); *A61B 2017/07214* (2013.01); *A61B 2017/347* (2013.01); *A61B 2090/0813* (2016.02)

(58) Field of Classification Search
CPC ............... A61B 17/068; A61B 17/072; A61B 17/07207; A61B 17/00234; A61B 17/115; A61B 17/1155; A61B 2017/07214; A61B 2017/00477; A61B 2017/07271
USPC .... 227/19, 175.2, 176.1; 606/139, 153, 213, 606/219
See application file for complete search history.

(56) References Cited

U.S. PATENT DOCUMENTS

| | | | |
|---|---|---|---|
| 3,193,165 | A | 7/1965 | Akhalaya et al. |
| 3,388,847 | A | 6/1968 | Kasulin et al. |
| 3,552,626 | A | 1/1971 | Astafiev et al. |
| 3,638,652 | A | 2/1972 | Kelley |
| 3,771,526 | A | 11/1973 | Rudie |

(Continued)

FOREIGN PATENT DOCUMENTS

| | | |
|---|---|---|
| CA | 908529 A | 8/1972 |
| DE | 1057729 B | 5/1959 |

(Continued)

OTHER PUBLICATIONS

European Search Report dated Feb. 13, 2017, issued in DP Application No. 16190284.

*Primary Examiner* — Scott A Smith
(74) *Attorney, Agent, or Firm* — Carter, DeLuca & Farrell LLP

(57) ABSTRACT

An adapter assembly for connecting a loading unit to a handle assembly is provided. The adapter assembly includes a sleeve, a trocar assembly releasably securable with the sleeve, and a locking mechanism configured to releasably secure the trocar assembly within the sleeve.

12 Claims, 12 Drawing Sheets

(56) References Cited

U.S. PATENT DOCUMENTS

| | | |
|---|---|---|
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |

(56) References Cited

U.S. PATENT DOCUMENTS

| | | |
|---|---|---|
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,419,495 B2 | 9/2008 | Menn et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,665,647 B2 | 2/2010 | Shelton, IV et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,901,416 B2 * | 3/2011 | Nolan ............... A61B 17/1114 227/175.1 |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |

(56) References Cited

U.S. PATENT DOCUMENTS

| | | | |
|---|---|---|---|
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,348,122 B2 * | 1/2013 | Milliman ............ A61B 17/115 |
| | | | 227/175.1 |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,360,296 B2 * | 1/2013 | Zingman ............ A61B 17/072 |
| | | | 227/175.2 |
| 8,365,974 B2 | 2/2013 | Milliman |
| 8,393,514 B2 | 3/2013 | Shelton, IV et al. |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,573,461 B2 | 11/2013 | Shelton, IV et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,045 B2 | 12/2013 | Smith et al. |
| 8,608,047 B2 | 12/2013 | Holsten et al. |
| 8,613,383 B2 * | 12/2013 | Beckman ............ A61B 17/115 |
| | | | 227/175.1 |
| 8,616,428 B2 | 12/2013 | Milliman et al. |
| 8,616,429 B2 | 12/2013 | Viola |
| 8,622,275 B2 | 1/2014 | Baxter, III et al. |
| 8,627,995 B2 * | 1/2014 | Smith ................ A61B 17/1114 |
| | | | 227/179.1 |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Milliman |
| 8,770,460 B2 * | 7/2014 | Belzer ................ A61B 17/115 |
| | | | 227/179.1 |
| 9,023,014 B2 | 5/2015 | Chowaniec et al. |
| 10,111,684 B2 | 10/2018 | Williams |
| 2003/0111507 A1 | 6/2003 | Nunez |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0147432 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0253329 A1 | 10/2012 | Zemlok et al. |
| 2012/0273548 A1 | 11/2012 | Ma et al. |
| 2012/0325888 A1 | 12/2012 | Qiao et al. |
| 2013/0015232 A1 | 1/2013 | Smith et al. |

(56) References Cited

U.S. PATENT DOCUMENTS

| | | |
|---|---|---|
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0000411 A1 | 1/2014 | Shelton, IV et al. |
| 2014/0008413 A1 | 1/2014 | Williams |
| 2014/0012317 A1 | 1/2014 | Orban et al. |
| 2016/0361057 A1* | 12/2016 | Williams ............ A61B 17/068 |

FOREIGN PATENT DOCUMENTS

| | | |
|---|---|---|
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2524656 A2 | 11/2012 |
| EP | 3011915 A1 | 4/2016 |
| EP | 3103402 A1 | 12/2016 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 9621119 A1 | 7/1996 |
| WO | 0154594 A1 | 8/2001 |
| WO | 2008107918 A1 | 9/2008 |
| WO | 2012166468 A1 | 12/2012 |

* cited by examiner

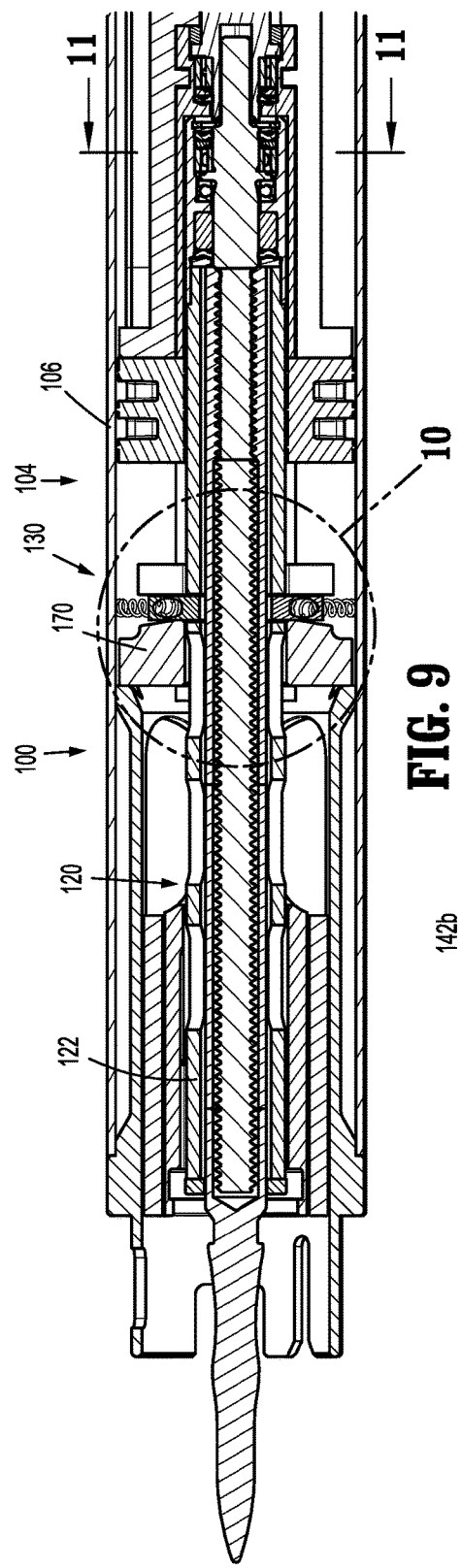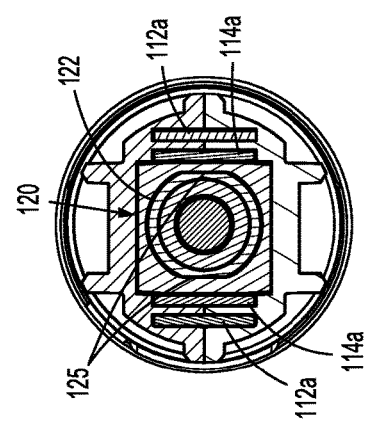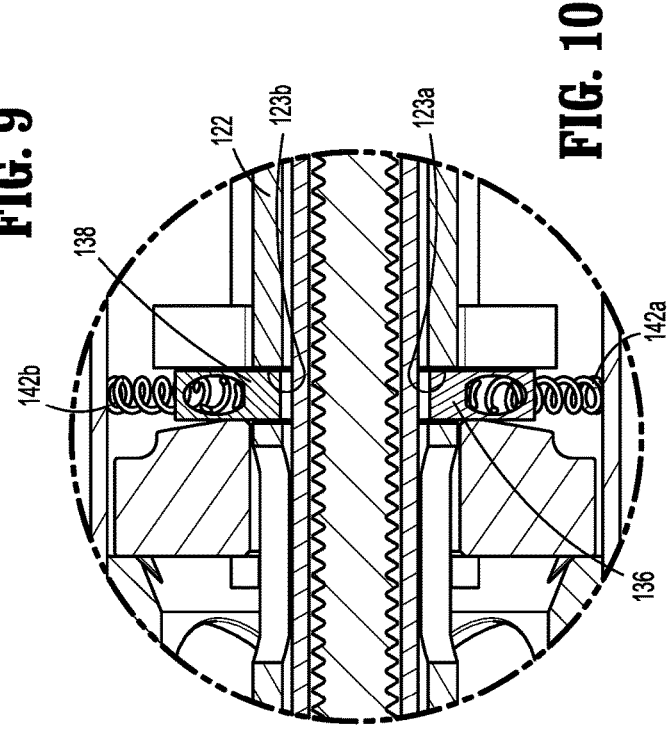
FIG. 9
FIG. 11
FIG. 10 ns ADAPTER ASSEMBLY INCLUDING A
REMOVABLE TROCAR ASSEMBLY

CROSS-REFERENCE TO RELATED APPLICATIONS

The present application is a Continuation Application which claims that benefit of and priority to U.S. patent application Ser. No. 14/865,602, filed on Sep. 25, 2015, now U.S. Pat. No. 10,111,684, the entire content of which is incorporated herein by reference.

BACKGROUND

Technical Field

The present disclosure relates to reusable surgical stapling devices. More particularly, the present disclosure relates to reusable adapter assemblies including a removable trocar assembly for use with a circular stapler.

Background of Related Art

Surgical devices for applying staples, clips, or other fasteners to tissue are well known. Typically, endoscopic stapling devices include an actuation unit, i.e., a handle assembly for actuating the device and a shaft for endoscopic access, and a tool assembly disposed at a distal end of the shaft. In certain of these devices, the shaft includes an adapter assembly, having a proximal end securable to the handle assembly and a distal end securable to the tool assembly. The adapter assembly may include an extension.

The adapter assembly may be reusable. To facilitate sterilization and cleaning of the adapter assembly, it would be beneficial to have an adapter assembly including a removable trocar assembly.

SUMMARY

An adapter assembly for connecting a loading unit to a handle assembly is provided. The adapter assembly includes a sleeve, a trocar assembly releasably securable with the sleeve, and a locking mechanism configured to releasably secure the trocar assembly within the sleeve. The trocar assembly includes a housing defining first and second locking slots. The locking mechanism includes first and second locking members configured for selective reception within the respective first and second locking slots of the trocar housing.

In embodiments, the first and second locking members are moveable between a first position where the trocar assembly is securely received within the sleeve and a second position where the trocar assembly is removable from within the sleeve. The locking mechanism may include a button member for moving the first and second locking members between the first position and the second position. The first and second locking members may be biased to the first position by respective first and second springs. The first and second locking members may maintain the button member in an outward position when the first and second locking members are in the first position.

In some embodiments, the adapter assembly includes upper and lower band guides. First and second block members may be movably supported on the upper and lower band guides. The adapter assembly may further include inner and outer flexible band assemblies. The upper and lower band guides may each define a longitudinal recess for accommodating the inner and outer flexible band assemblies. The locking mechanism may further include a button member. The button member may be operably secured to the upper band guide. Each of the upper and lower band guides may include a pair of cam posts for operably supporting the first and second locking members.

In one embodiment, the adapter assembly may further include a base, and a handle rotatably secured to the base. A proximal end of the sleeve may be fixedly secured to the handle to permit rotation of the sleeve.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure, wherein:

FIG. 9 is a cross-sectional top view taken along section line 9-9 shown in FIG. 8, with first and second locking blocks of the locking mechanism in a locked position;

FIG. 10 is an enlarged view of the indicated area of detail shown in FIG. 9;

FIG. 11 is a cross-sectional end view taken along section line 11-11 shown in FIG. 9;

DETAILED DESCRIPTION

Figure 1:
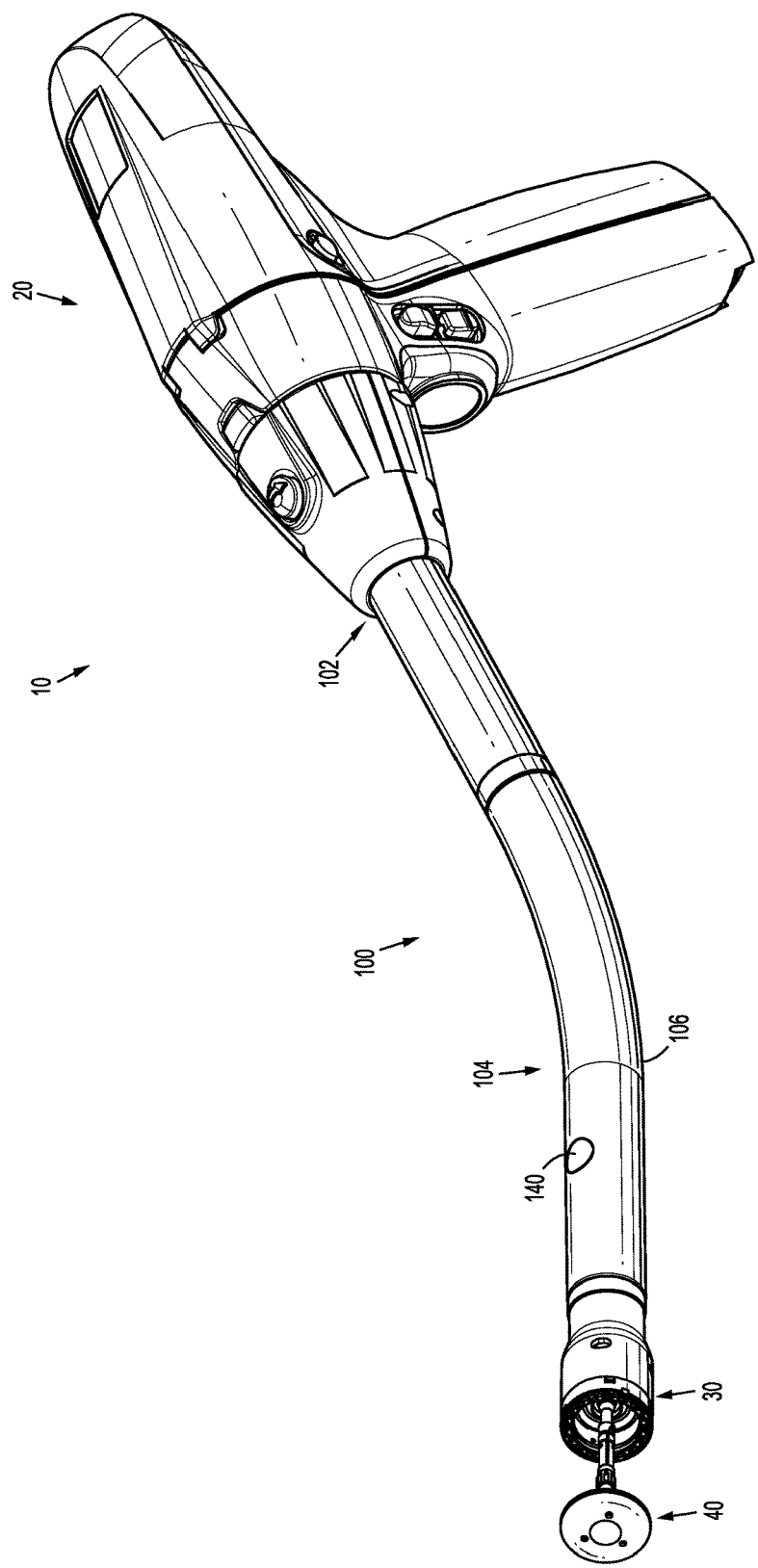
FIG. 1 is a perspective view of a surgical stapling device including an handle assembly with an adapter assembly according to one embodiment of the present disclosure.

Embodiments of the presently disclosed adapter assembly including a removable trocar assembly will now be described in detail with reference to the drawings in which like reference numerals designate identical or corresponding elements in each of the several views. As is common in the art, the term "proximal" refers to that part or component closer to the user or operator, i.e. surgeon or clinician, while the term "distal" refers to that part or component further away from the user.

Referring initially to FIG. 1, an adapter assembly according to an embodiment of the present disclosure, shown generally as adapter assembly 100, is a component of a surgical stapling device 10. The surgical stapling device 10 further includes a powered handle assembly 20, a loading unit 30, and an anvil assembly 40. Although shown and described with reference to surgical stapling device 10, the aspects of the present disclosure may be modified for use with manual surgical stapling devices having various configurations, and with powered surgical stapling devices having alternative configurations. For a detailed description of an exemplary surgical stapling device, please refer to commonly owned U.S. Pat. No. 9,023,014 ("the '014 patent) and U.S. Pat. Appl. Publ. No. 2012/0253329 ("the '329 application"), the contents of each of which are incorporated by reference herein in their entirety.

Figure 2:
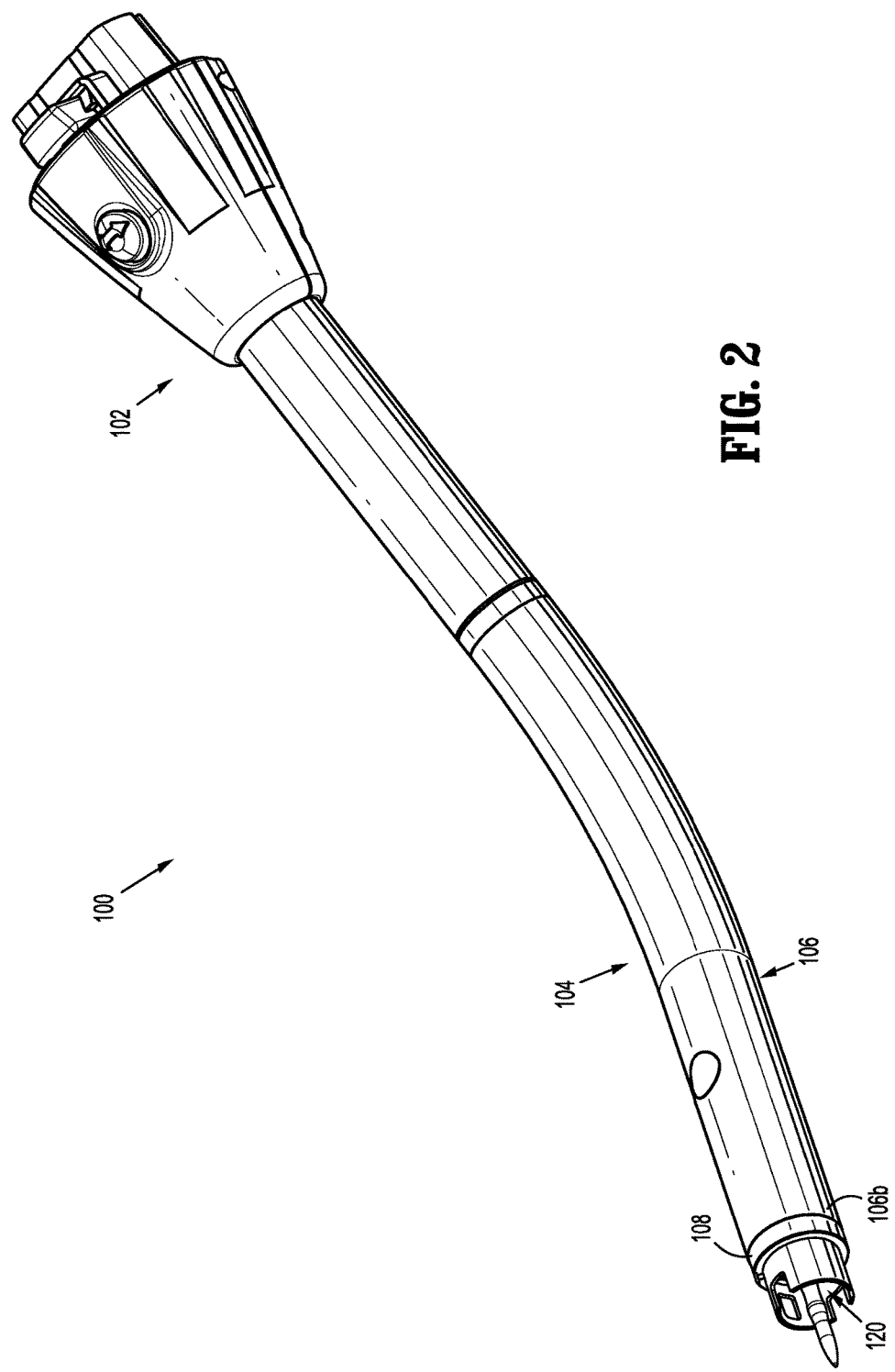
FIG. 2 is a perspective view of the adapter assembly shown in FIG. 1 with a removable trocar assembly extending from a distal end of the adapter assembly.

With reference to FIG. 2, the adapter assembly 100 includes a proximal portion 102 configured for operable connection to the handle assembly 20 (FIG. 1) and a distal portion 104 configured for operable connection to the loading unit 30 (FIG. 1) and to the anvil assembly 40 (FIG. 1). Although shown and described as forming an integral unit, it is envisioned that the proximal and distal portions 102, 104 may be formed as separate units that are releasably securable to one another.

The adapter assembly 100 will only be described to the extent necessary to fully disclose the aspects of the present disclosure. For a detailed description of an exemplary adapter assembly, please refer to commonly owned U.S. Provisional Pat. Appl. Ser. No. 62/066,518 ("the '518 application"), the content of which is incorporated by reference herein in its entirety.

With continued reference to FIG. 2, the adapter assembly 100 includes an outer sleeve 106, and a connector housing 108 secured to a distal end of the outer sleeve 106. The connector housing 108 is configured to releasably secure an end effector, e.g., the end effector 30 (FIG. 1), to the adapter assembly 100.

Figure 3:
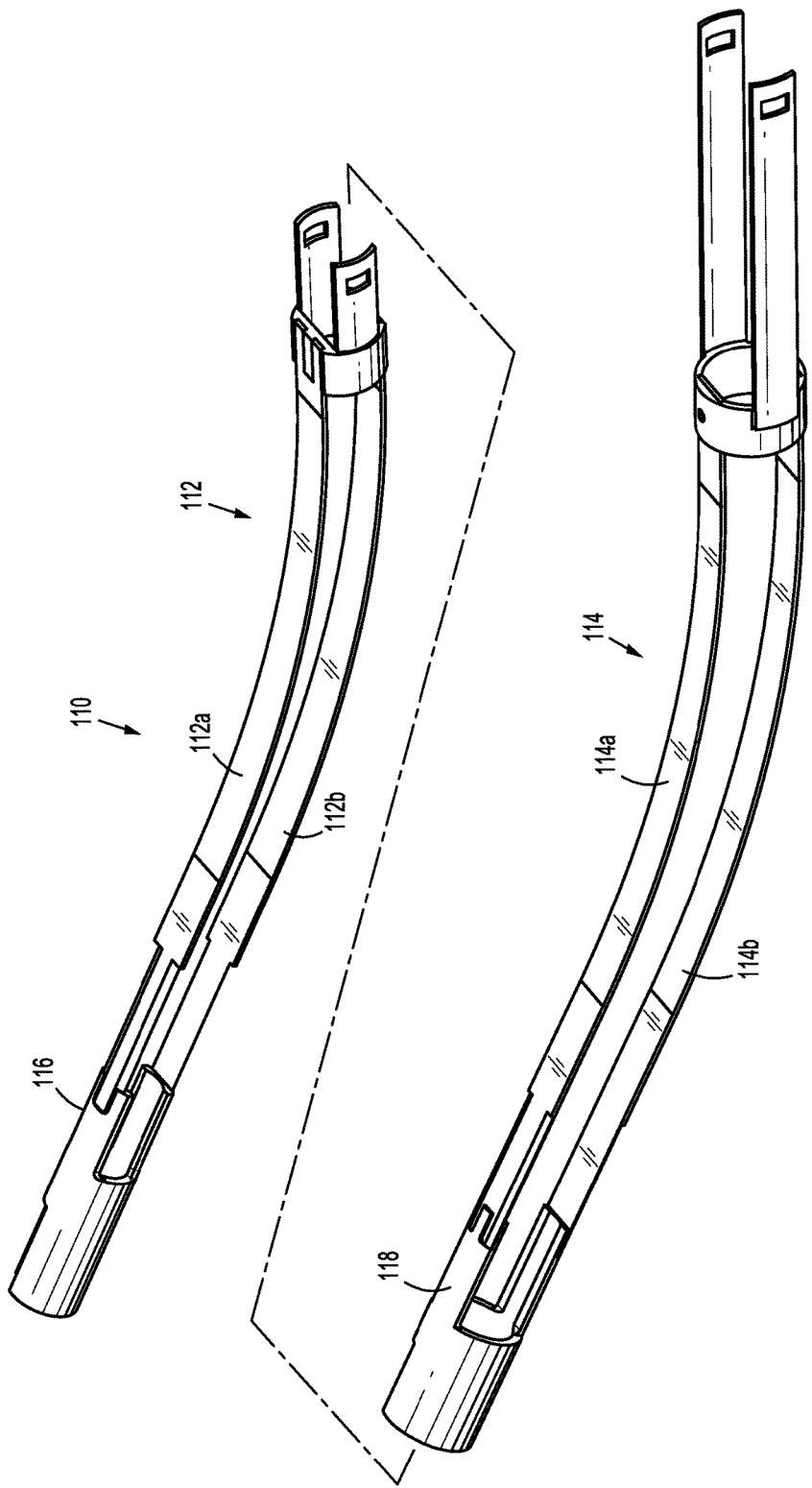
FIG. 3 is a perspective view of a drive assembly of the adapter assembly shown in FIG. 1 with components separated.

Turning briefly to FIG. 3, a drive assembly 110 extends through the outer sleeve 106 (FIG. 2) of the adapter assembly 100, and includes an inner flexible band assembly 112 and an outer flexible band assembly 114. The inner flexible band assembly 112 includes first and second flexible bands 112a, 112b, and an inner pusher member 116 connected to the distal ends of the first and second flexible bands 112a, 112b. Similarly, the outer flexible band assembly 114 includes first and second flexible bands 114a, 114b, and an outer pusher member 118. For a detailed description of the structure and function of the drive assembly 110, please refer to the '518 application, the content of which was previously incorporated herein by reference in its entirety.

Figure 4:
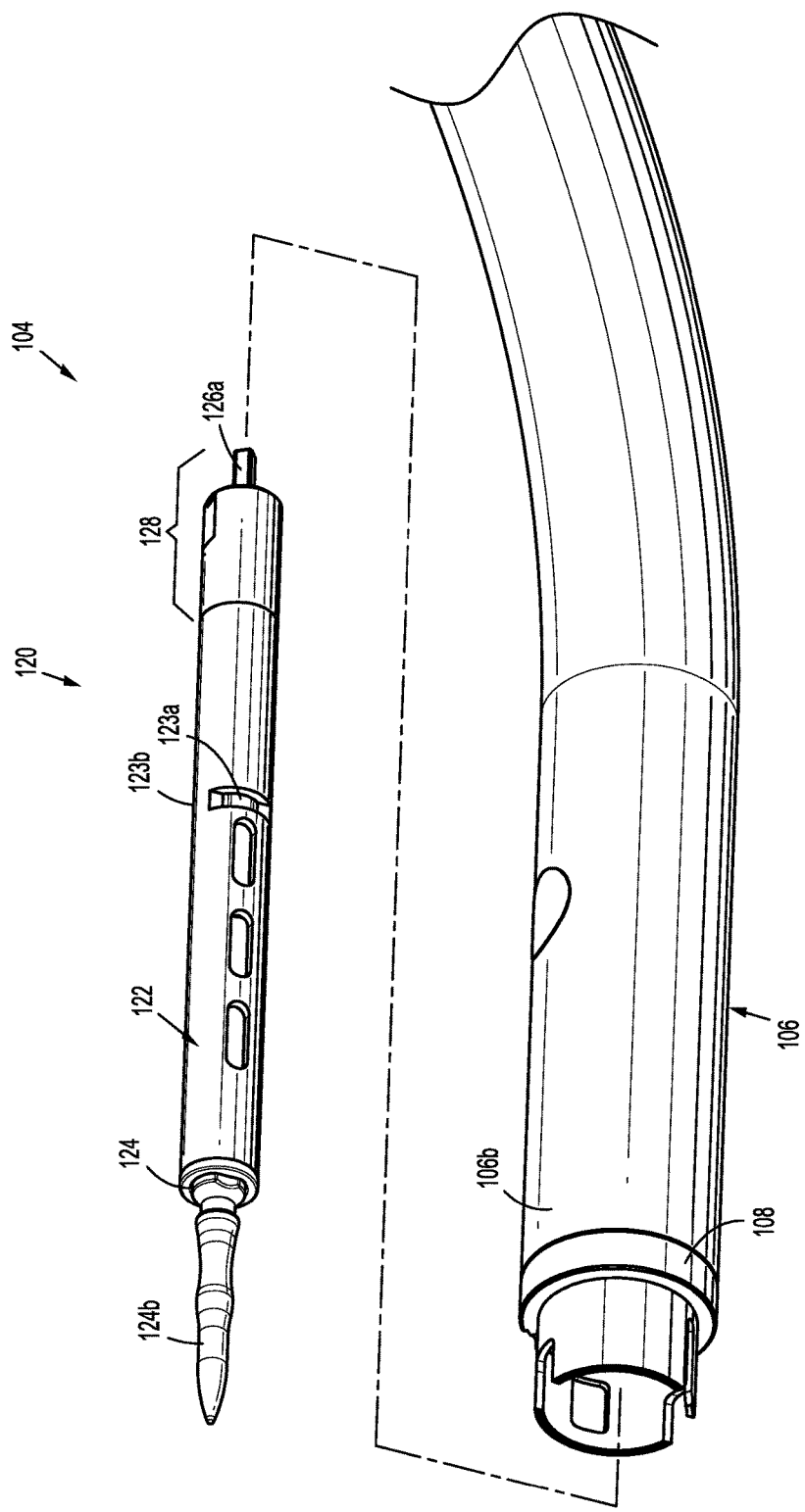
FIG. 4 is a side perspective view of the removable trocar assembly, a sleeve, and a connector housing of the adapter assembly shown in FIG. 1, with components separated.
Figure 5:
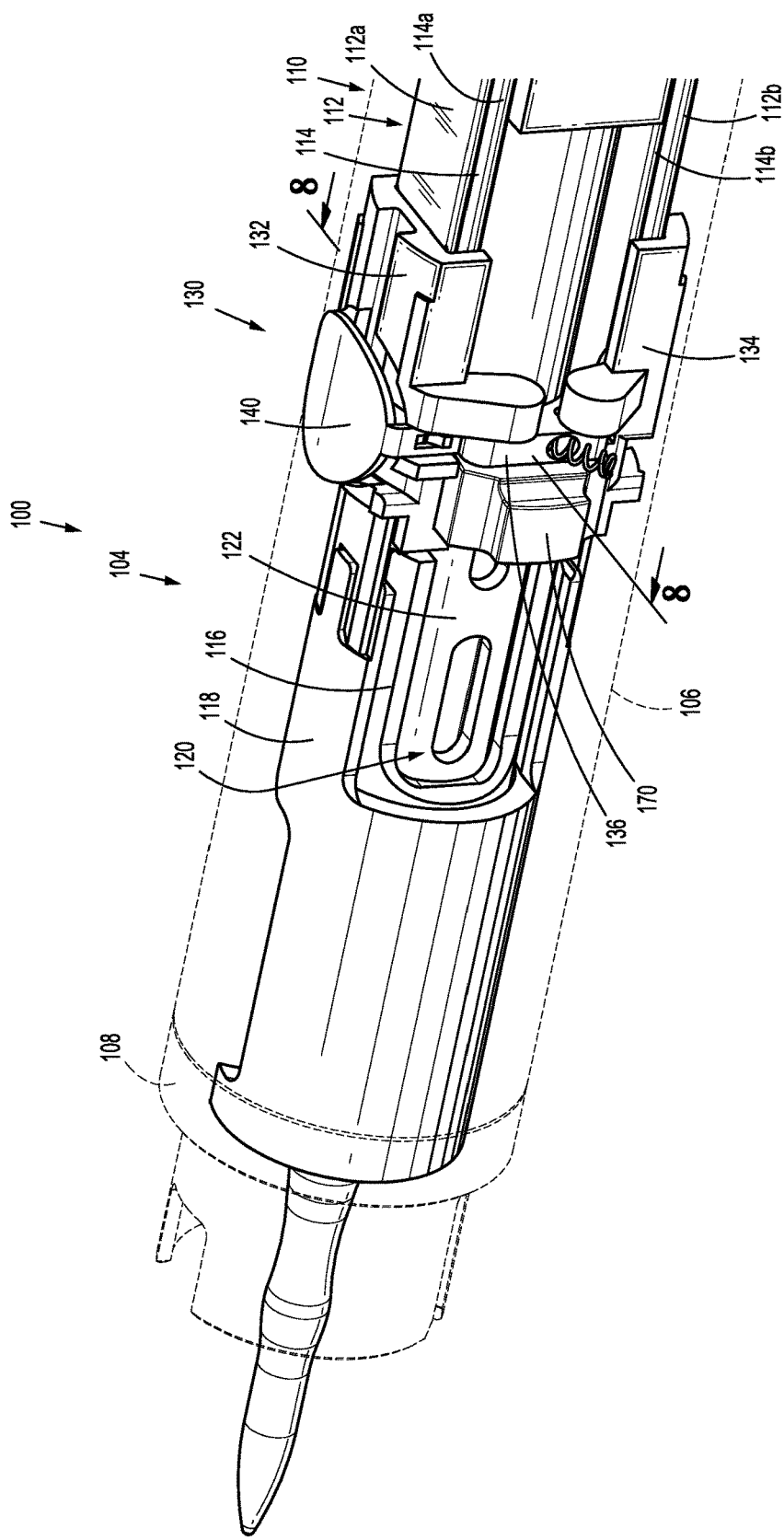
FIG. 5 is a side perspective view of a distal end of the adapter assembly shown in FIG. 1, with the sleeve shown in phantom.

With reference now to FIGS. 4 and 5, the adapter assembly 100 further includes a trocar assembly 120 that extends through the actuation assembly 110 (FIG. 5), and a locking mechanism 130 (FIG. 5) that releasably secures the trocar assembly 120 relative to the outer sleeve 106 of the adapter assembly 100. The trocar assembly 120 will only be described to the extent necessary to describe the aspects of the present disclosure. For a detail description of the structure and function of an exemplary trocar assembly, please refer to the '518 application, the content of which was previously incorporated by reference herein in its entirety.

Figure 6:
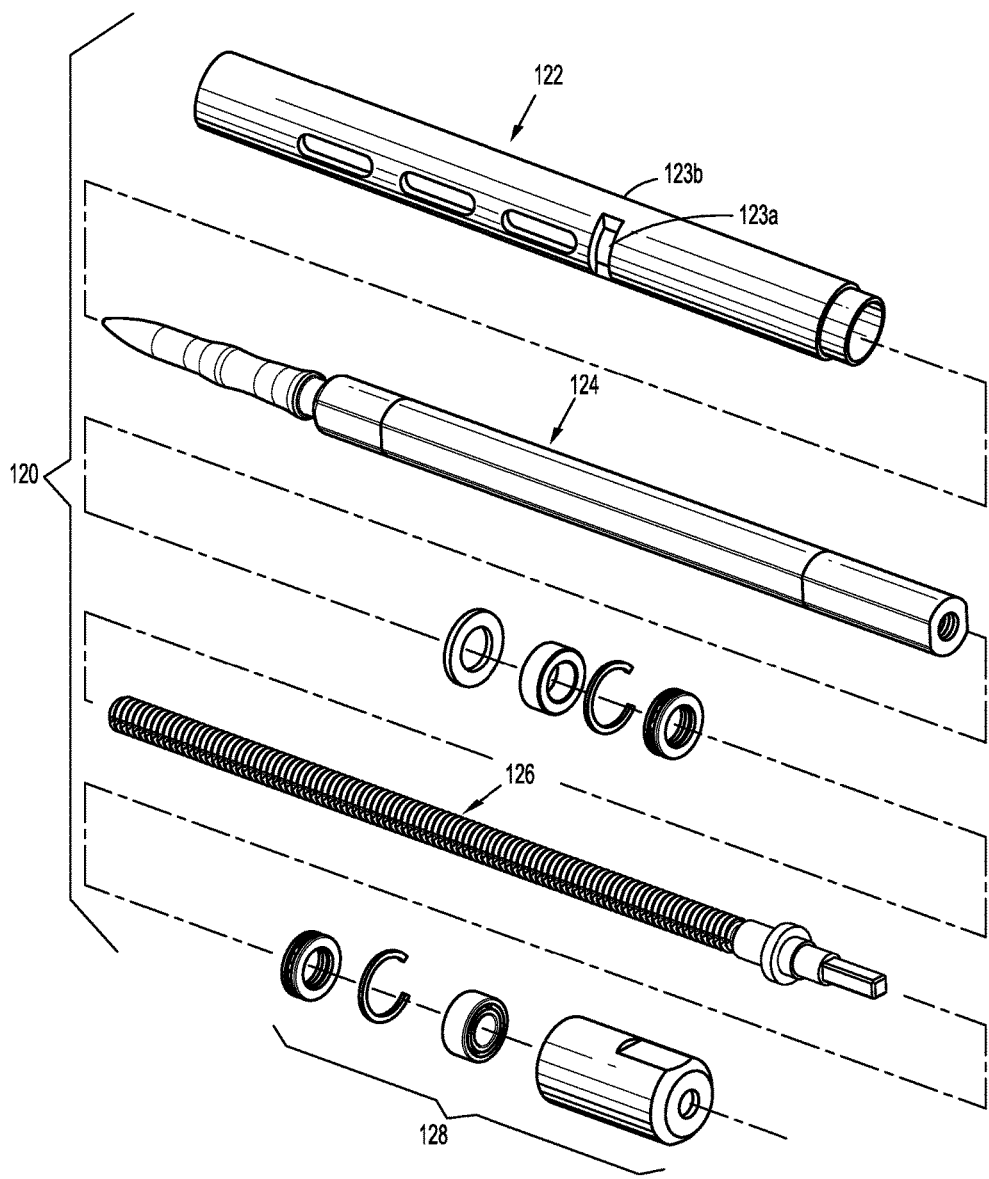
FIG. 6 is a perspective view of the removable trocar assembly shown in FIG. 4, with parts separated.

Referring also to FIG. 6, the trocar assembly 120 of the adapter assembly 100 (FIG. 2) includes an outer housing 122, a trocar member 124 slidably disposed within the outer housing 122, and a drive screw 126 operably received within the trocar member 124 for axially moving the trocar member 124 relative to the outer housing 122. More specifically, the trocar member 124 defines a threaded bore 124a which is dimensioned to receive the drive screw 126. The outersurface of the drive screw 126 is threaded such that rotation of the drive screw 126 causes longitudinal movement of the trocar member 124 within the outer housing 122 of the trocar assembly 120. A distal end 124b of trocar member 124 is configured to releasably engage an anvil assembly, e.g., the anvil assembly 40 (FIG. 1). A bearing assembly 128 is mounted to a proximal end of outer housing 122 of trocar assembly 120 for rotatably supporting the drive screw 126 within the outer housing 122 and the trocar member 124. As will be described in further detail below, the outer housing 122 defines first and second locking slots 123a, 123b for receiving the respective first and second locking blocks 136, 138 (FIG. 7) of the locking mechanism 130 of the adapter assembly 100.

Figure 7:
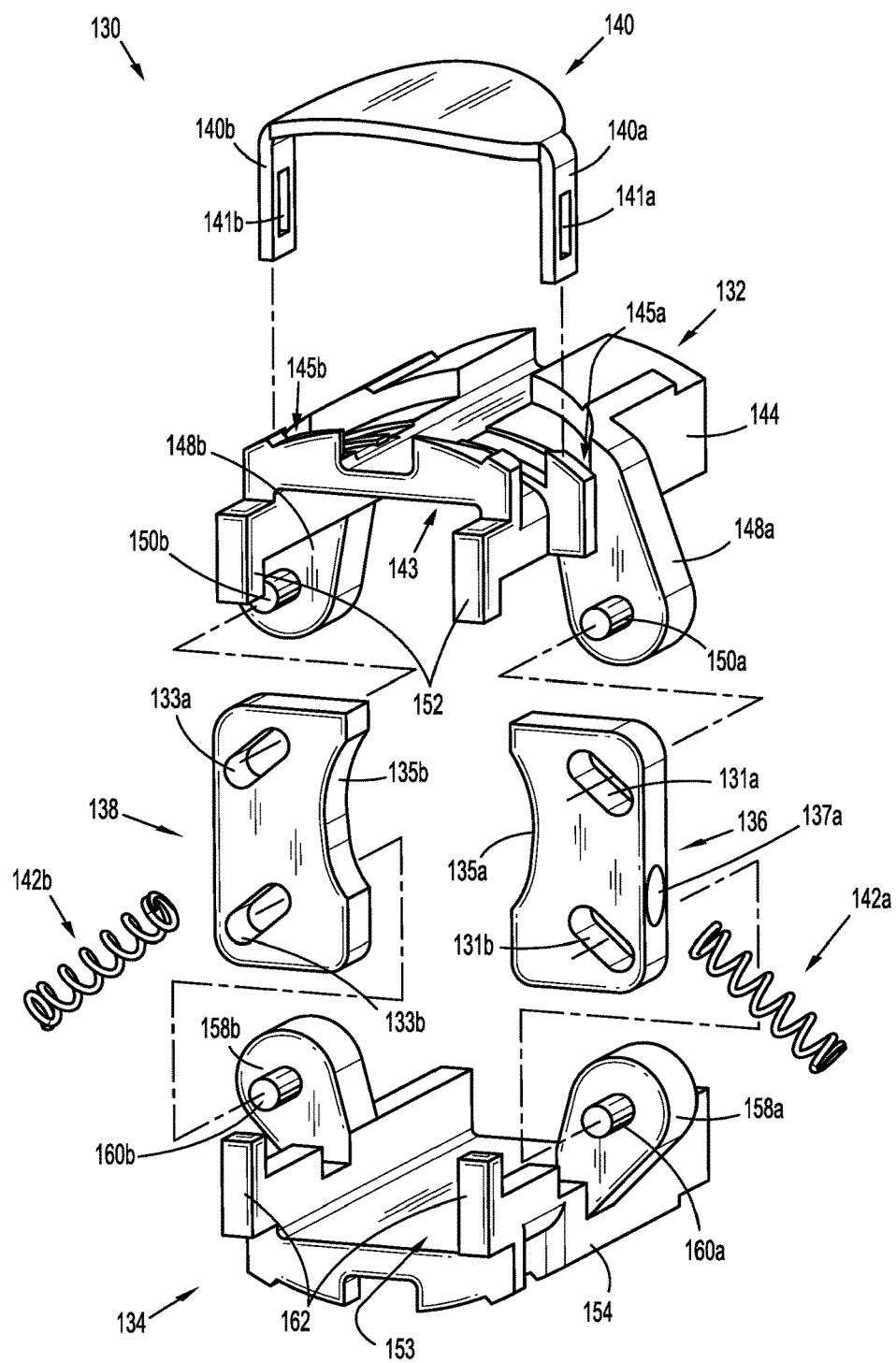
FIG. 7 is a side perspective view of a locking mechanism of the adapter assembly shown in FIG. 1, with parts separated.

With particular reference now to FIG. 7, the locking mechanism 130 of the adapter assembly 100 includes upper and lower band guides 132, 134 supported within the outer sleeve 106 (FIG. 5), first and second locking blocks 136, 138 operably supported on each of the upper and lower band guides 132, 134, and a button member 140 slidably secured to the upper band guide 132 for moving the first and second locking blocks 136, 138 relative to each other. As will be described in further detail below, first and second springs 142a, 142b extend from within respective first and second locking blocks 136, 138 and bias the locking blocks 136, 138 radially inward.

With continued reference to FIG. 7, the upper band guide 132 of the locking mechanism 130 includes a body portion 144 disposed within the outer sleeve 106 of the adapter assembly 100. The body portion 144 of the upper band guide 132 defines a longitudinal recess 143 for accommodating the first flexible bands 112a, 114a of the respective inner and outer flexible band assemblies 112, 114. The body portion 144 of the upper band guide 132 further defines first and second cutouts 145a, 145b for operably receiving respective first and second legs 140a, 140b of the button member 140 of the locking mechanism 130. First and second button retainer tabs 146a, 146b (FIG. 12) extend outwardly from the body portion 144 of the upper band guide 132. In particular, the first button retainer tab 146a is disposed in the first cutout 145a of the body portion 144 and the second button retainer tab 146b is disposed in the second cutout 145b of the body portion 144.

Figure 8:
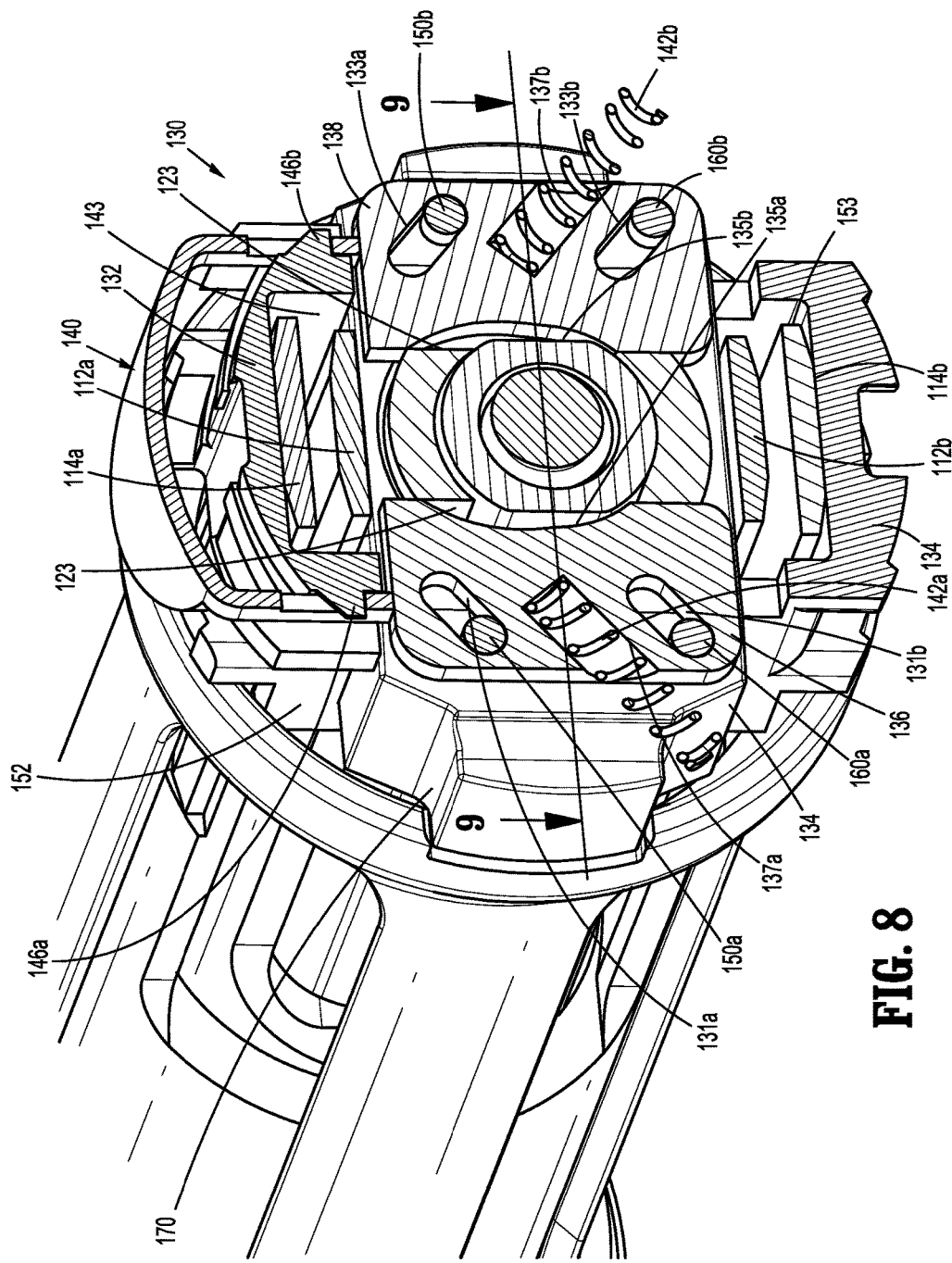
FIG. 8 is a cross-sectional perspective view taken along section line 8-8 shown in FIG. 5.

As will be described in further detail below, the first and second button retainer tabs 146a, 146b are received within respective slots 141a, 141b of the button member 140 to operably secure the button member 140 to the upper guide band 132. First and second flange portions 148a, 148b extend outwardly from the body portion 144 of the upper band guide 132. Each of the first and second flange portions 148a, 148b includes a cam post 150a, 150b, respectively. As will be described in further detail below, the cam posts 150a, 150b of the respective first and second flange portions 148a, 148b are received within first and second cam slots 131a, 131b and 133a, 133b of first and second locking blocks 136, 138. The upper band guide 132 further includes strain gauge retainer portions 152 extending from the body portion 144 for supporting a strain gauge 170 (FIG. 8).

With continued reference to FIG. 7, the lower band guide 134 of the locking mechanism 130 includes a body portion 154 disposed within the outer sleeve 106 (FIG. 1) of the adapter assembly 100. The body portion 154 of the lower band guide 134 defines a longitudinal recess 153 for accommodating the second inner and outer flexible bands 112b, 114b (FIG. 3) of the respective inner and outer flexible band assemblies 112, 114 (FIG. 3). The lower band guide 134 includes first and second flange portions 158a, 158b that extend outwardly from the body portion 154. The first and second flange portions 158a, 158b include first and second cam posts 160a, 160b, respectively. The lower band guide 134 further includes strain gauge retainer portions 162 extending from the body portion 144 configured to operate with the strain gauge retainer portions 152 of the upper band guide 132 to support the strain gauge 170 (FIG. 8) about the trocar assembly 120.

As will be described in further detail below, the upper and lower band guides 132, 134 of the locking mechanism 130 are configured such that the first cam posts 150a, 160a of the respective upper and lower band guides 132, 134 are received within first cam slots 131a, 131b of the first locking block 136 and the second cam posts 150b, 160b of the respective upper and lower band guides 132, 134 are received within the second cam slots 133a, 133b of the second locking block 138. With additional reference to FIG. 8, the first and second locking blocks 136, 138 of the locking mechanism 130 are movably supported on the upper and lower band guides 132, 134 and are configured to be releasably received within the respective first and second locking slots 123a, 123b (FIG. 6) of the trocar housing 122 of the trocar assembly 120.

Figure 14:
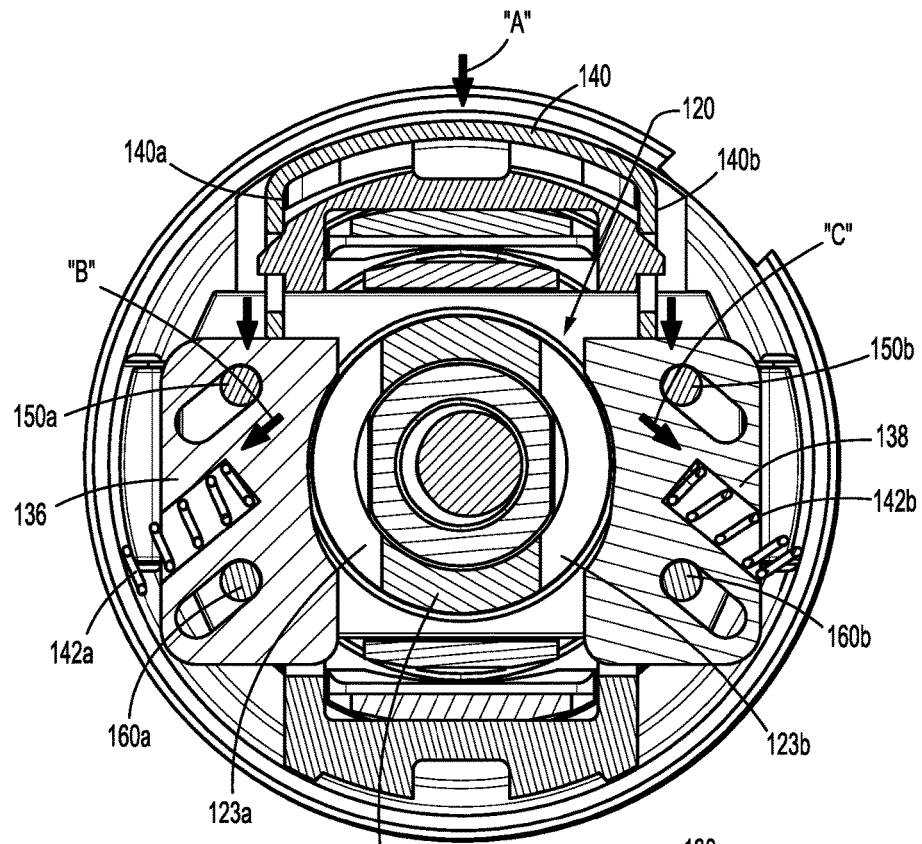
FIG. 14 is a cross-sectional view taken along respective section lines 8-8 shown in FIG. 5, with the locking mechanism in a second or release position.

Each of the first and second locking blocks 136, 138 defines a clearance portions 135a, 135b, respectively, to facilitate disengagement of the respective first and second locking blocks 136, 138 from the trocar assembly 120. In particular, the clearance portions 135a, 135b are configured such that when the first and second locking blocks 136, 138 are in their second positions (FIGS. 14 and 15), the first and second locking blocks 136, 138 are clear of the outer housing 122 of the trocar assembly 120. As shown in FIG. 14, the clearance portions 135a, 135b of the respective first and second locking blocks 136, 138 together define a substantially circular opening with the first and second locking blocks 136, 138 are in their second position. Each of the first and second locking blocks 136, 138 further defines a bore 137a, 137b (FIG. 8), respectively, for receiving the first and second springs 142a, 142b.

The first and second locking blocks 136, 138 of the locking mechanism 130 are movable between a first, locked position (FIG. 12) in which the outer housing 122 of the trocar assembly 120 is engaged by the first and second locking blocks 136, 138, i.e., portions of the first and second locking blocks 136, 138 are received within respective locking slots 123a, 123b of the outer housing 122, and a second, unlocked position (FIG. 14) in which the trocar assembly 120 is moved outwardly from slots 123a, 123b such that is removable from between the first and second locking blocks 136, 138 of the locking mechanism 130, i.e., the clearance portions 135a, 135b of the respective first and second blocks 136, 138 are aligned with the outer housing 122. The first and second locking blocks 136, 138 are biased inwardly into slots 123a, 123b to the first position by the first and second springs 142a, 142b. As shown in FIG. 8, the first and second locking blocks 136, 138 are biased upwardly and inwardly towards one another.

With particular reference still to FIG. 7, the button member 140 of the locking mechanism 130 includes first and second legs 140a, 140b each defining a slot 141a, 141b, respectively. The button member 140 is configured to be received about the upper band guide 132 of the locking mechanism 130 such that the first and second legs 140a, 140b of the button member 140 are received within respective first and second cutouts 145a, 145b of the upper band guide 132 and the first and second tabs 146a, 146b (FIG. 8) of the upper band guide 134 are received within the respective slots 141a, 141b.

Figure 12:
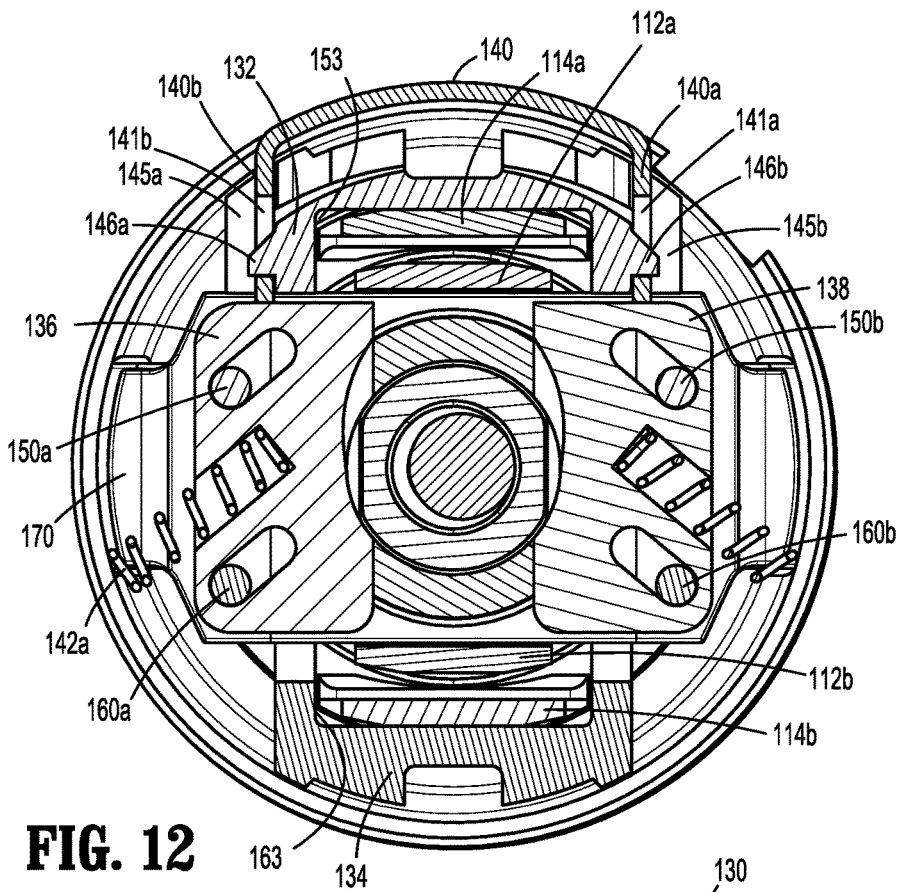
FIG. 12 is a cross-sectional view taken along section lines 8-8 shown in FIG. 5, with the locking mechanism in a first or locked position.
Figure 13:
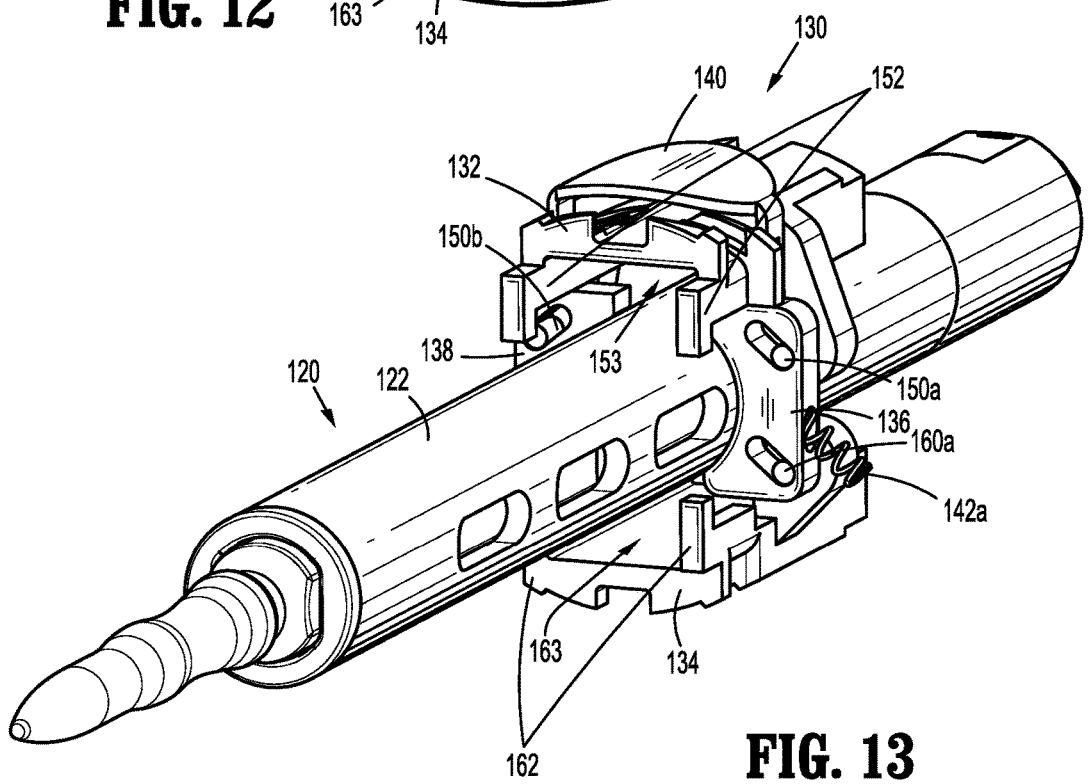
FIG. 13 is a perspective side view of the removable trocar assembly and the locking mechanism of the adapter assembly shown in FIG. 1, in the locked position.

The operation of the locking mechanism 130 of the adapter assembly 100 will now be described with reference to FIGS. 8-16. Referring initially to FIGS. 8-13, the locking mechanism 130 is shown in the locked configuration, i.e., with the first and second locking blocks 136, 138 in their first position. In particular, the first locking block 136 is supported on the first cam post 150a of the upper band guide 132 and the first cam post 160b of the lower band guide 134 and the second locking block 138 is supported on the second cam post 150b of the upper band guide 132 and the second cam post 160b of the lower band guide 134. The first and second locking blocks 136, 138 are biased radially inward by respective first and second springs 142a, 142b to the first, locked position (FIG. 12).

The trocar assembly 120 of adapter assembly 100 may be provided preloaded within sleeve 106 of the adapter assembly 100, or the trocar assembly 120 may be provided separated from the adapter assembly 100. If provided as a separate component, the trocar assembly 120 is loaded through a distal end of the sleeve 106 of the adapter assembly 100 prior to attaching an end effector, e.g., the end effector 30, to the connector housing 108 of the adapter assembly 100. The trocar assembly 120 is fed into the sleeve 106 of the adapter assembly 100 between the first and second locking blocks 136, 138 to cam the first and second locking blocks 136, 138 outwardly against the bias of springs 142a, 142b until alignment of the first and second locking blocks 136, 138 with the first and second locking slots 123a, 123b of the outer housing 122. An audible and/or tactile indication may be provided to a user by the locking mechanism 130 as the first and second locking blocks 136, 138 are received with the respective first and second locking slots 123a, 123b to indicate that the trocar assembly 120 is securely received within the locking mechanism 130.

During loading of the trocar assembly 120 through the locking mechanism 130, the button member 140 of the locking mechanism 130 may be depressed to move the first and second locking blocks to the second or unlocked position (FIG. 14) to facilitate loading of the trocar assembly 120 between the first and second locking blocks 136, 138, and within the sleeve 106. Alternatively, engagement of the first and second locking blocks 136, 138 by the outer housing 122 of the trocar assembly 120 as the trocar assembly 120 is loaded through the locking mechanism 130 will maintain the first and second locking blocks 136, 138 in their second position until the first and second locking slots 123a, 123b of the outer housing 122 align with the respective first and second locking blocks 136, 138. Upon alignment of the first and second locking blocks 136, 138 with the respective first and second locking slots 123a, 123b, the first and second locking blocks 136, 138 are biased into the first and second locking slots 123a, 123b, respectively.

In embodiments, the outer housing 122 of the trocar assembly 120 includes internal flat portions 125 (FIG. 11) for maintaining rotational alignment of the trocar assembly 120 relative to the locking mechanism 130 to ensure that the first and second locking slots 123a, 123b of the trocar assembly 120 are maintained in alignment with the respective first and second locking blocks 136, 138 of the locking mechanism 130.

Engagement of the first and second legs 140a, 140b of the button member 140 of the locking mechanism 130 with the respective first and second locking blocks 136, 138 maintains the button member 140 in an outward, non-depressed position. Receipt of the first and second button retainer tabs 146a, 146b within respective slots 141a, 141b of the first and second leg 140a, 140, respectively, of button member 140 maintains the button member 140 in engagement with the upper band guide 132 of the locking mechanism 130.

As noted above, the upper and lower band guides 132, 134 each include strain gauge retainer portions 152, 162, respectively, for supporting the strain gauge 170. The trocar assembly 120 of the adapter assembly 100 is received through the strain gauge 170. The strain gauge 170 is configured to measure deflection and/or movement of the trocar assembly 120 during operation of the adapter assembly 100. The first and second flexible bands 112a, 114a of the inner and outer flexible band assemblies 112, 114 of the drive assembly 110 are received through the longitudinal recess 143 of the upper band guide 132 and the first and second flexible bands 112a, 114b of the inner and outer flexible band assemblies 112, 114 are received through the longitudinal recess 153 of the lower band guide 134.

Once the trocar assembly 120 is loaded with the sleeve 106 and secured therein by the locking mechanism 130, the adapter assembly 100 and the attached handle assembly 20 (FIG. 1), the loading unit 30, and the anvil assembly 40 (FIG. 1) operate in a traditional manner.

Following a surgical stapling procedure using the surgical stapling device 10, the trocar assembly 120 of the adapter assembly 100 is removed from the sleeve 106 of the adapter assembly 100 to facilitate cleaning and/or sterilizing of the adapter assembly 100.

Figure 15:
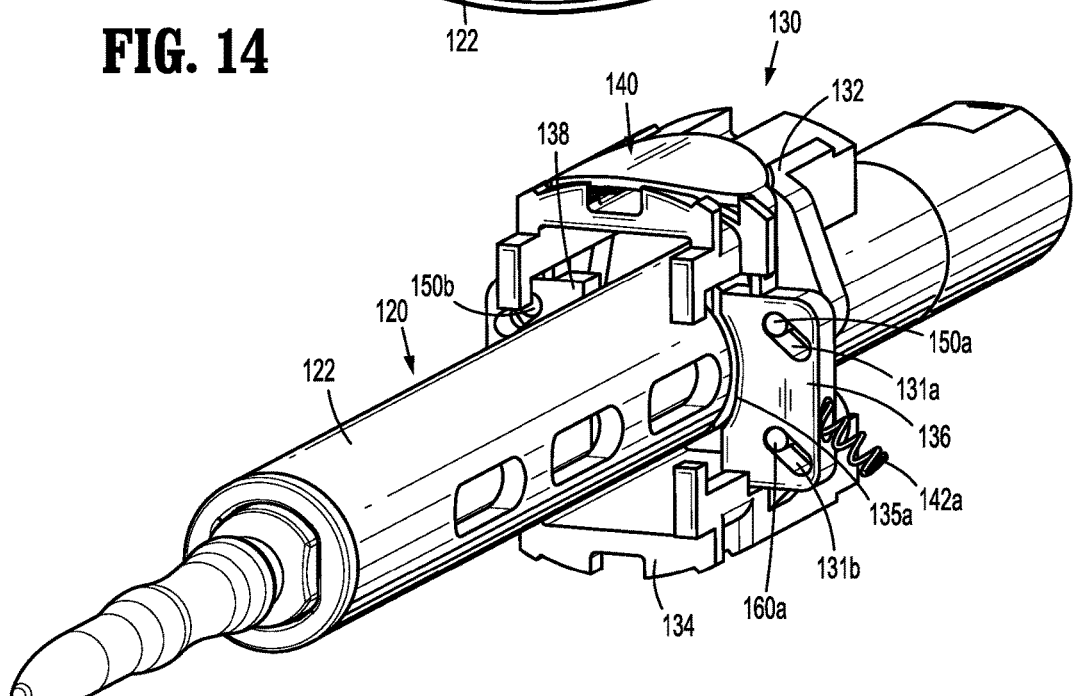
FIG. 15 is a perspective side view of the removable trocar assembly and the locking mechanism shown in FIG. 13, in the release position.
Figure 16:
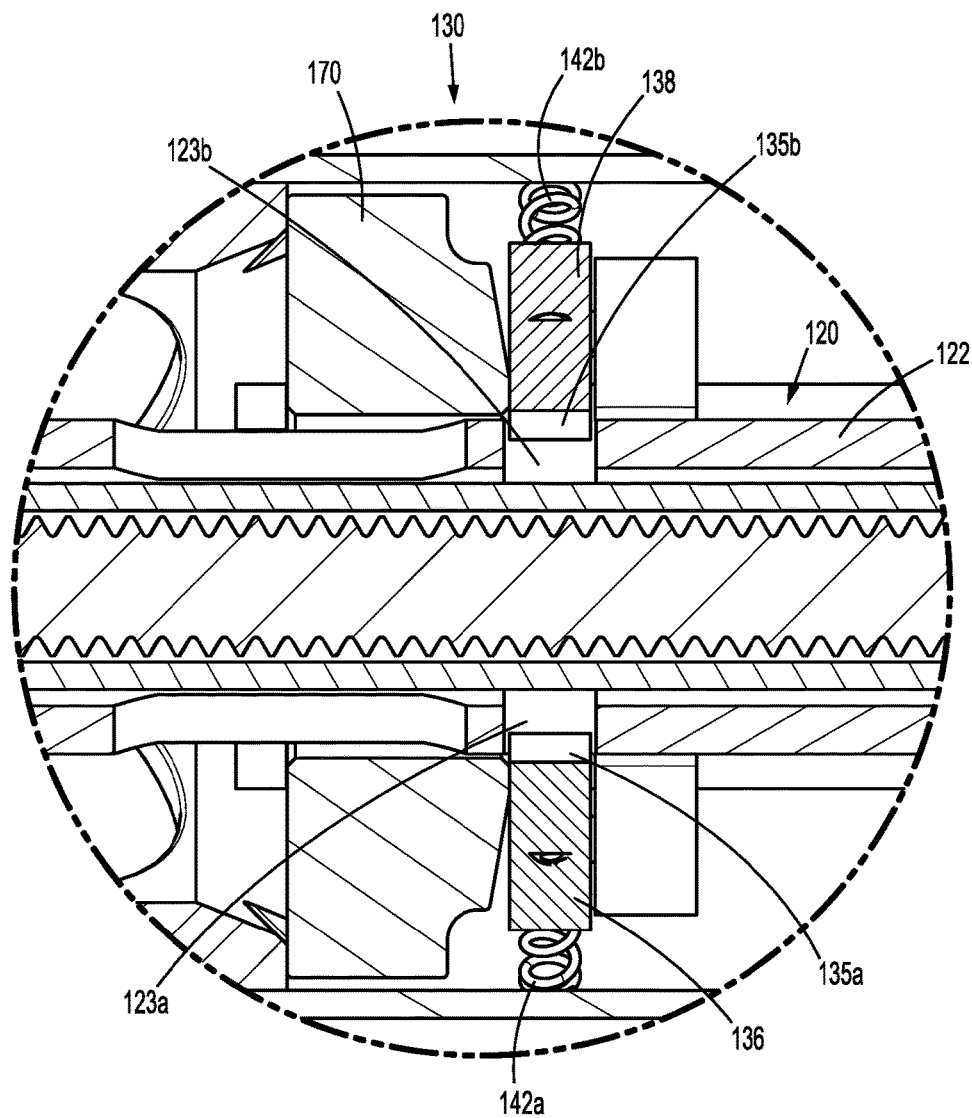
FIG. 16 is a cross-sectional top view taken along section line 9-9 shown in FIG. 8, with first and second locking blocks of the locking mechanism in an unlocked position.

With reference to FIGS. 14-16, the locking mechanism 130 of the adapter assembly 100 is shown with the first and second locking blocks 136, 138 in a second or unlocked position. When the first and second locking blocks 136, 138 are in the second position, the trocar assembly 120 is removable from within the sleeve 106 of the adapter assembly 100.

With particular reference to FIG. 14, the first and second locking blocks 136, 138 are moved to the second position by depressing the button member 140 of the locking mechanism 130 radially inward, as indicated by arrow "A" in FIG. 14. As noted above, the first and second leg portions 140a, 140b of the button member 140 engage an upper surface of the respective first and second locking blocks 136, 138. When the button member 140 is depressed, engagement between the first and second leg portions 140a, 140b of the button member 140 with the respective first and second locking blocks 136, 138 moves the first and second locking blocks 136, 138 downwardly about the cam posts 150a, 160a and 150b, 160b against the bias of the first and second springs 142a, 142b, respectively. The first locking block 136 rides along the first cam post 150a, 160a of the upper and lower band guide 132, 134, respectively. Because of the configuration of the cam slots 131a, 131b, the first locking block 136 moves in a radially outward direction, as indicated by arrow "B" to the second position. Similarly, the second locking block 138 rides along the second cam post 150b, 160b of the upper and lower band guide 132, 134, respectively. Because of the configuration of the cam slots 133a, 133b, the second locking block 138 moves in a radially outward direction, as indicated by arrow "C", to the second position.

As the first and second locking blocks 136, 138 are moved to their second position, the first and second locking blocks 136, 138 are moved from within the respective first and second locking slots 123a, 123b of the trocar assembly 120 and the clearance portions 135a, 135b of the respective first and second locking blocks 136, 138 are aligned with the trocar assembly 120. In this manner, the trocar assembly 120 is no longer secured by the locking mechanism 130. The trocar assembly 120 may then be removed from within the sleeve 106 of the adapter assembly 100.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure. For example, in any of the embodiments discussed herein, the trocar assembly may form part of a circular surgical stapler that is wholly or partially disposable and such instruments may have a separate adapter or the adapter may be formed as part of the handle assembly. The stapling instrument can be manually operated, powered through an integral or separate motor, or form part of a robotic system.

What is claimed is:

1. An adapter assembly for connecting a loading unit to a handle assembly, the adapter assembly comprising:
 a sleeve;
 a trocar assembly releasably securable within the sleeve, the trocar assembly including a trocar housing and a trocar member selectively extendable from the trocar housing, the trocar housing defining a first locking slot; and
 a locking mechanism configured to releasably secure the trocar assembly within the sleeve, the locking mechanism including a first locking member configured for selective reception within the first locking slot of the trocar housing.

2. The adapter assembly of claim 1, wherein the first locking member is moveable between a first position where the trocar assembly is secured within the sleeve and a second position where the trocar assembly is removable from within the sleeve.

3. The adapter assembly of claim 2, wherein the locking mechanism further includes a button member for moving the first locking member between the first position and the second position.

4. The adapter assembly of claim 3, wherein the first locking member is biased to the first position by a first spring.

5. The adapter assembly of claim 4, wherein the at least first locking member maintains the button member in an outward position when the first locking member is in the first position.

6. The adapter assembly of claim 1, further including upper and lower band guides and a first block member, wherein the least first block member is movably supported on the upper and lower band guides.

7. The adapter assembly of claim 6, further including inner and outer flexible band assemblies, wherein the upper and lower band guides each define a longitudinal recess for accommodating the inner and outer flexible band assemblies.

8. The adapter assembly of claim 6, wherein the locking mechanism further includes a button member, wherein the button member is operably secured to the upper band guide.

9. The adapter assembly of claim 6, wherein each of the upper and lower band guides include a cam post for operably supporting the first locking member.

10. The adapter assembly of claim 1, further including a base and a handle rotatably secured to the base, wherein a proximal end of the sleeve is fixedly secured to the handle to permit rotation of the sleeve.

11. The adapter assembly of claim 1, further including a loading unit, wherein a plurality of staples is arranged in a circular array within the loading unit.

12. The adapter assembly of claim 1, wherein the trocar member includes a distal portion configured for releasable engagement with an anvil assembly.

* * * * *